United States Patent [19]

Imbert

[11] Patent Number: 4,875,480
[45] Date of Patent: * Oct. 24, 1989

[54] DEVICE FOR TRANSLUMINAL IMPLANTATION

[75] Inventor: Christian Imbert, Preverenges, Switzerland

[73] Assignee: Medinvent S.A., Lausanne, Switzerland

[*] Notice: The portion of the term of this patent subsequent to Mar. 22, 2005 has been disclaimed.

[21] Appl. No.: 100,784

[22] Filed: Sep. 25, 1987

[30] Foreign Application Priority Data

Sep. 30, 1986 [SE] Sweden ................................. 8604145

[51] Int. Cl.⁴ ............................................. A61M 25/00
[52] U.S. Cl. .................................... 128/343; 128/344; 623/1; 623/12; 604/53
[58] Field of Search ................ 128/341, 342, 343, 344, 128/334 R, 334 C; 604/45, 43, 53; 623/1, 11, 12

[56] References Cited

U.S. PATENT DOCUMENTS 4,445,892  5/1984  Hussein et al. ....................... 128/344
4,503,569  3/1985  Dotter ............................. 128/334 R
4,732,152  3/1988  Wallsten et al. ....................... 623/1

Primary Examiner—Richard J. Apley
Assistant Examiner—David S. Isabella
Attorney, Agent, or Firm—Burns, Doane, Swecker & Mathis

[57] ABSTRACT

A device for implantation by insertion into a difficulty accessible location of a substantially tubular, radially expandable prosthesis including in combination such prosthesis and concentric therewith a flexible probe provided with an arrangement for maintaining said prosthesis in a radially contracted state and for releasing same at the desired location. The arrangement includes a hose concentrically surrounding the probe and radially surrounding the prosthesis to form a compartment therefor. The probe has a central axial channel enabling supply of a liquid flushing medium at its other end and the probe is provided with at least one radial aperture opening into the prosthesis compartment to enable flushing of the prosthesis compartment to remove gases therefrom before implantation.

20 Claims, 2 Drawing Sheets

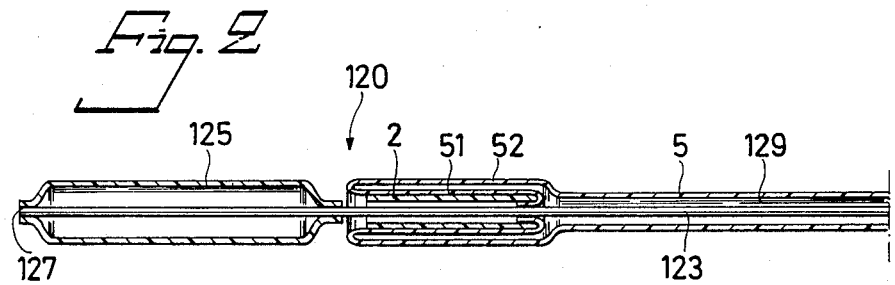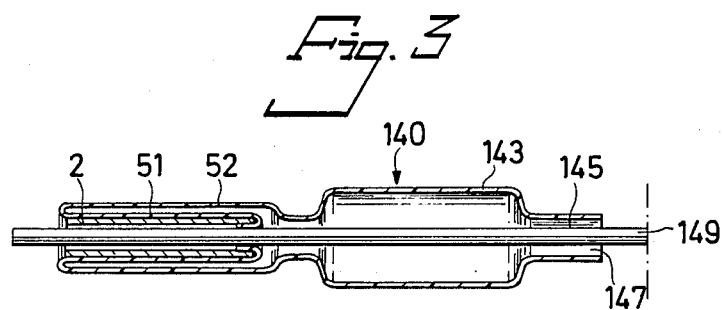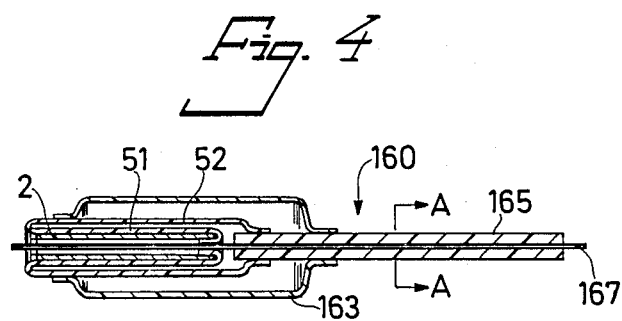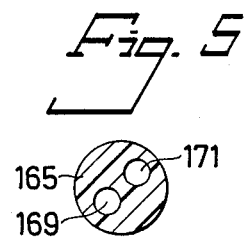

DEVICE FOR TRANSLUMINAL IMPLANTATION

TECHNICAL AREA

The invention relates to a device for transluminal implantation of a substantially tubular, expandable and preferably selffixing implant, such as a graft or prosthesis.

BACKGROUND

Published PCT-application WO/SE85/00503 describes a device for transluminal implantation comprising a substantially tubular, radially expandable prosthesis, the device comprising in combination such prosthesis and concentric therewith a flexible probe with means for maintaining said prosthesis in a radially contracted state and for releasing same at the desired location. The said means for maintaining and releasing the prosthesis comprises a hose concentrically surrounding the probe, one end of said hose being connected to the probe and the hose being folded inside itself to form a double-walled section radially surrounding the prosthesis to form a compartment therefor. The prosthesis is releasable by axial relative movement of the ends of the hose.

In preferred embodiment of the device of said PCT-application the hose is leaktight and both ends thereof are tightly connected to the probe. Furthermore, the surface of the probe adjacent to the hose is leaktight between the endconnections of the hose, whereby the hose and the probe form a chamber that can be pressurized using a liquid whereby the liquid reduces the contact pressure between the hose walls of the double-walled section thereby reducing the friction between the outer hose wall and the inner hose wall at axial relative movement between same.

ALthough this known device for transluminal implantation operates in an excellent manner when practically used it has been found in use that the prosthesis compartment after introduction of the prosthesis as a preparation for implantation contains gases, mostly air, that are intrapped in said compartment and within the thread elements of the prosthesis. Such gases may when releasing the prosthesis in for example a blood vessel, cause problems when released into the blood flow.

The invention has for its main purpose to alleviate said problem of gases contained in the prosthesis compartment. For said purpose the device according to the invention is characterized in that the probe has a central axial channel that can be used for supplying a liquid flushing medium at its other end. Flushing can take place without closing said channel at its front end but it can, if desired, be restricted or closed to improve the flushing efficiency. Furthermore, the probe is provided with at least one radial aperture opening into the prosthesis compartment to enable flushing of the prosthesis compartment to remove gase therefrom before implantation.

According to a preferred embodiment of the device of the invention several apertures are arranged in the probe substantially evenly distributed around the probe, and said apertures are preferably located behind the prosthesis as seen in the direction of the transluminal transfer of the device.

The invention also provides for means for eliminating the risk of possible release of gases present between the walls of the hose in its double-walled section in case of rupture of the hose within said section. For this purpose the device according to the invention is characterized by at least one small hole extending through the hose wall at the front end of the double-walled section to enable displacement by flushing of gases present between the walls of the hose in said double-walled section. The size of such hole is selected such that it enables escape of the gases but prevents or substantially reduces passage of the liquid used for pressurization. It is preferred to arrange several such holes at the front end of the double-walled section, and such plurality of holes is advantageously located substantially evenly distributed around the front end of said hose section. Although the size of such hole is dependent on the character of the liquid used for pressurizing chamber formed by the hose and the probe a suitable size lies between about 0.001 and 0.1 mm. When using isotonic saline solution as a pressurizing liquid a preferred diameter of the hole is about 0.05 mm.

For further details regarding the device according to the invention reference is made to the above-identified PCT-application, the full disclosure of which is incorporated herein by reference. The present invention will in the following be further described in the form on non-limiting examples of embodiments thereof, reference being had to the appended drawings.

DRAWINGS

FIG. 2 is a diagrammatic sideview of another embodiment of the device of the invention;

FIG. 3 is a diagrammatic sideview of yet another embodiment of the invention;

FIG. 4 is a diagrammatic sideview of still another embodiment of the invention; and FIG. 5 is a section taken along line AA in FIG. 4.

EXAMPLES OF EMBODIMENTS

Figure 1:
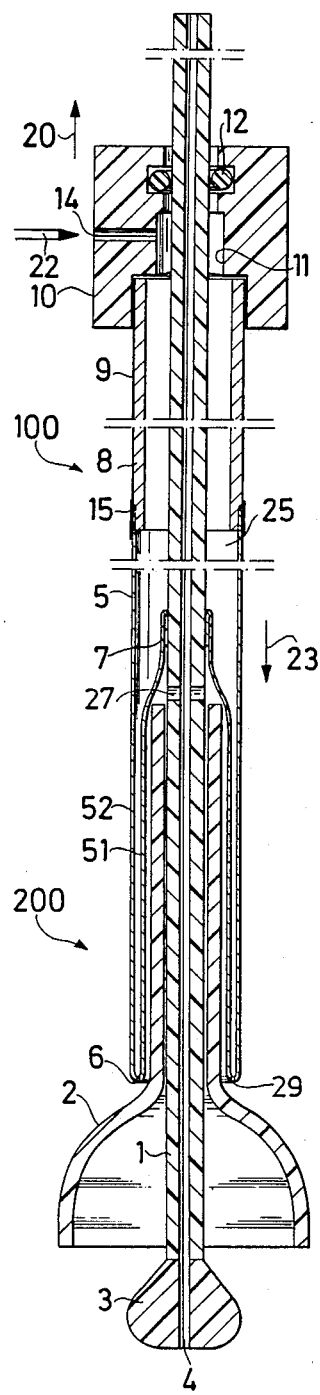
FIG. 1 shows diagrammatically an axial section through a device according to the invention.

In FIG. 1 there is shown a device for implantation of a so called expandable graft or prosthesis 2 in a living organism to a difficultly accessible location therein, for example a desired site of a vein or artery, graft 2 being intended to strengthen a defective section of the vein or artery.

Generally, the device includes a probe means 100 having at its insertion end means 200 to grip and carry a graft or prosthesis 2.

The device comprises an elongated flexible probe 1, having at least an axially through-going channel 4. The tube/probe 1 is flexible and consists for example of nylon. At its front end tube 1 is provided with a rounded head 3, through which the channel 4 continues. Head 3 serves to facilitate the insertion of the device through a narrow channel. A hose 5 is at its end 7 tightly and fixedly attached to the outer surface of tube 1. Hose 5 which is soft and for example consists of polyethylene or polyvinylchloride, is turned inside out to form a double-walled hose section, the inner wall of which as radially seen comprises said hose end 7. The graft 2 is a radially compressible element of tubular configuration surrounding the outer end of tube 1 and is surrounded by the double-walled section 51,52 of hose 5. By retracting the other end of hose 5 (upwardly in FIG. 1 relative to tube 1) the fold 6 of the double-walled hose section 51,52 moves along the hose towards the site of attachment of end 7 of hose 5. Thereby no sliding movement takes place between graft 2 and hose wall 51. Along with the movement of fold 6 upwardly in FIG. 1 graft 2 will be exposed in an axial direction and can expand to engagement against a vein or artery. Hose 5 is coaxially connected to a flexible manoeuvering tube consisting of a helix spring 8 of stainless steel, spring 8 being exteriorly covered by a removable tight enclosure of for example polyvinylchloride. PVC-enclosure 9 is tightly connected to the polyethylene tube by means of a joint 15. A bushing 10 surrounds tube 1 and is rigidly connected to the spring 8 and tightly connected to enclosure 9. The other end of the bushing has an O-ring seal 12 sealing against the outer surface of tube 1. Tube 1, hose 5, spring enclosure 9, bushing 10 and seal 12 thus form a closed chamber 25. Bushing 10 has a bore 14 extending through the wall of the bushing and forming a channel, through which a fluid 22, such as physiological saline solution, blood substitute, air or the like, can be introduced and pressurized in space 25. Hereby fluid 22 can penetrate in between hose walls 51,52 and separate same so that they at substantially reduced friction can move axially relative to each other.

Channel 4 of tube 1 can be used to introduce a contrast fluid 21 to the area around the front end of the device so that the position of the device may be easily detected, for example using X-ray technique.

To release graft 2 the operator can using one hand hold the aft end of tube 1 and using the other hand retract bushing 10 in the direction of arrow 20, the fold 6 of hose 5 being retracted so as to release graft 2.

In FIG. 1 the direction of insertion of the device is indicated by arrow 23.

For the purposes of the present invention tube 1 is provided with a number of radially extending holes or apertures 27 providing passages between channel 4 of tube 1 and the rear end of the compartment accomodating prosthesis 2.

In practical use of the device of the invention it has been found that gases will remain in said compartment within and without prosthesis 2. The device described makes it possible to remove such gases from said compartment preferably by blocking channel 4 at the front end of tube 1 and introducing a suitable liquid at arrow 21 at the other end of the tube. Such liquid, which could be for example isotonic saline solution or a contrast liquid will flow through channel 4 and passages 27 displacing the gases contained in the prosthesis compartment within the double-walled section 51, 52. After such removal of the gases the implantation device is in order for implantation.

The device shown in FIG. 1 further comprises small holes 29 provided at the front end of the double-walled section 51,52. These holes make it possible to remove gases, such as air, contained in space 25. By introducing suitable pressurizing liquid at 22 through a bore 14 the gasescontaining space 25 can be displaced through holes 29 to completely fill space 25 with pressurizing liquid. Holes 29 have a size selected such that the gases can pass therethrough, whereas the pressurizing liquid cannot. In this manner any risk for release of gases into the blood flow in case of rupture of hose 5 will be eliminated.

FIGS. 2 to 5 of the appended drawings relate to embodiments of the device of the invention including in addition to the feature of enabling implantation of an expandable graft or prosthesis also means for dilatation of a stenosis in a vessel or lumen before implanting a supporting graft serving as a stent to prevent restenosis. In theses figures holes 27 and 29 are not shown but they function in the same manner as described in connection with FIG. 1.

FIG. 2 is a diagrammatic sideview of such an embodiment of the device of the invention. The device comprises a central tubing 123 surrounded by a flexible hose 5 including the double-walled section 51,52. The radially compressed graft 2 is as described before positioned inside the double-walled section 51,52 and surrounding the central tubing 123.

At the front end of central tubing 123 there is arranged a dilatation balloon 125 sealingly attached at both ends to the central tubing 123.

While not shown in detail in the drawing balloon 125 can be pressurized separately from the double-walled section 51,52 by pressurizing the central passage 127 of tubing 123. The double-walled section 51,52 can be pressurized by introducing a pressure medium in the annular space 129 formed between tubing 123 and the surrounding hose 5.

In operation the device shown in FIG. 2 functions briefly as follows.

After insertion of the device generally designated 120 into the desired location of for example a blood vessel, balloon 125 is inflated by separate pressurization of same. This inflation of the balloon has for a purpose to widen the lumen at the location of the stenosis and where graft 2 is later to be implanted.

After widening the lumen at the desired location balloon 125 is deflated and the device 120 moved forward so that the double-walled section 51,52 thereof takes the proper position in the vessel. By relative movement between central tubing 123 and hose 5 in an axial direction graft 2 can now be released at the desired location in the vessel to provide for permanent reinforcement of the vessel whereby for example restenosis can be avoided. After the implantation the device 120 is then removed from the vessel.

The embodiment shown in FIG. 3 performs the same functions as that of FIG. 2, but the dilatation ballooned is positioned behind the double-walled section 51,52. In this embodiment the inflation of the double-walled section 51,52 to avoid friction is performed using the same pressure medium as used for inflating balloon 143 due to the communicating passage therebetween. The function of the device of FIG. 3 is otherwise the same as that of FIG. 2 the same advantages being obtained.

In FIG. 4 there is shown an embodiment where balloon 163 is arranged so as to surround the double-walled section 51,52. This embodiment designated 160 contains a central wire or thread 167 surrounded by a hose 165. Surrounding the hose 165 there is arranged a balloon 163 sealingly attached to the hose at the aft end and to the front part of the outer wall 52.

To provide for separate pressurization of the balloon and the double-walled section 51,52 there is arranged within hose 165 two internal passages 169,171, as shown in FIG. 5 in an enlarged cross section. Passage 169 can be used for accomodating the central wire 167 and for pressurizing the double-walled section 51,52 to reduce friction. Passage 171 can be used for pressurizing the dilatation balloon 163 separately from the double-walled section 51,52. It is, of course, possible to arrange for three internal passages within hose 165, two for individual pressurization and one for a central guidewire. This arrangement can, of course, also be used in the embodiments of FIGS. 2 and 3. In all embodiments involving balloon means separate pressurizing can be used for the said means and for the inflation of the double-walled section.

The function of the device shown in FIG. 4 is the same as that of the devices shown in FIGS. 2 and 3 with the difference that no axial displacement of the device has to be performed after widening the lumen using the balloon 163 since the position of widening the lumen is juxtaposed to the graft or prosthesis 2 accomodated within the double-walled section 51,52.

The prosthesis used in the device of this invention can be of any type as long as it is radially expandable to provide for radial expansion and self-fixation when released in a vessel or other tract. A particularly preferred prosthesis or graft is described in into the prosthesis compartment to enable flushing of the prosthesis compartment to remove gases therefrom before implantation. U.S. Pat. No.4,655,771, which was issued on Apr. 7, 1987, 4,655,771, which was issued on Apr. 7, 1987, the disclosure of which is incorporated herein by reference. This prosthesis or graft comprises a flexible tubular body which is composed of several individual rigid but flexible thread elements each of which extends in helix configuration with the centerline of the body as a common axis, a number of elements having the same direction of winding but being axially displaced relative to each other crossing a number of elements also axially displaced relative to each other but having the opposite direction of winding. the diameter of such prosthesis or graft is variable by axial movement of the ends of the body relative to each other.

I claim:

1. A device for implantation by insertion into a difficulty accessible location of a substantially tubular, radially expansible prosthesis, including in combination said radially expandable prosthesis surrounding and concentric with a flexible probe and means for maintaining said prosthesis in a radially contracted state and for releasing said expandable prosthesis in the difficulty accessible location, said means for maintaining and releasing the prosthesis comprising a hose concentrically surrounding said probe and radially surrounding the prosthesis to form a compartment therefor with one end of the hose being connected to the probe, wherein the probe has a central axial channel enabling supply of a liquid flushing medium at one end and the probe is provided with at least one radial aperture opening into a compartment of the prosthesis to enable flushing of the prosthesis compartment to remove gases therefrom before implantation of the prosthesis.

2. A device according to claim 1, wherein a plurality of apertures in the probe are substantially evenly distributed around the probe, said apertures preferably located between said one end of the hose and the prosthesis.

3. A device according to claim 1, wherein the hose is folded inside itself to form a double-walled section, said double-walled section radially surrounding the prosthesis.

4. A device according to claim 3, wherein the hose is leaktight with both ends of the hose tightly connected to the probe and the surface of the probe adjacent to the hose is leaktight between the end-connections of the hose, whereby the hose and the probe form a chamber and pressurizing means are arranged for pressurizing a liquid in the chamber, the liquid flushing medium reduces contact pressure between the hose walls of the double-walled section thereby reducing friction between an outer hose wall and an inner hose wall during axial relative movement between the outer hose wall and the inner hose wall, at least one hole extending through the hose wall at a front end of the double-walled section to enable displacement by the flushing of gases present between the walls of the hose in the double-walled section, said hole being of such size that it enables escape of the gases but substantially reduces passage of the liquid used for pressurization.

5. A device according to claim 4, wherein the outer wall of the double-walled section is inflatable to ensure widening of the lumen before implanting the prosthesis.

6. A device according to claim 3, including inflatable balloon means positioned ahead of the double-walled section for widening the lumen before implanting the prosthesis.

7. A device according to claim 3, including inflatable balloon means arranged around the double-walled section substantially coextensive therewith.

8. A device according to claim 3, including inflatable balloon means positioned behind the double-walled section for widening the lumen before implanting the prosthesis.

9. A device according to claim 6, wherein said balloon means are independently operable for widening the lumen before implanting the prosthesis.

10. A device according to claim 1, wherein said axial channel is restricted at the front end thereof to improve efficiency of the flushing.

11. A device according to claim 1, wherein the prosthesis comprises a flexible tubular body which is composed of several individual rigid but flexible thread elements each of which extends in helix configuration with the centerline of the body as a common axis, a number of elements having the same direction of winding but being axially displaced relative to each other crossing a number of elements also axially displaced relative to each other but having the opposite direction of winding.

12. A device according to claim 2, wherein the hose is folded inside itself to form a double-walled section, said double-walled section radially surrounding the prosthesis.

13. A device according to claim 11, wherein the hose is leaktight with both ends of the hose tightly connected to the probe and the surface of the probe adjacent to the hose is leaktight between the end-connections of the hose, whereby the hose and the probe form a chamber and pressurizing means are arranged for pressurizing a liquid in the chamber, the liquid flushing medium reduces contact pressure between the hose walls of the double-walled section thereby reducing friction between an outer hose wall and an inner hose wall during axial relative movement between the outer hose wall and the inner hose wall, at least one hole extending through the hose wall at a front end of the double-walled section to enable displacement by the flushing of gases present between the walls of the hose in the double-walled section, said hole being of such size that it enables escape of the gases but substantially reduces passage of the liquid used for pressurization.

14. A device according to claim 2, wherein the hose forms a double-walled section and inflatable balloon means are positioned ahead of the double-walled section for widening the lumen before implanting the prosthesis.

15. a device according to claim 4, including inflatable balloon means positioned ahead of the double-walled section for widening the lumen before implanting the prosthesis.

16. A device according to claim 2, wherein the hose forms a double-walled section and inflatable balloon means are arranged around the double-walled section and substantially coextensive therewith.

17. A device according to claim 4, including inflatable balloon means arranged around the double-walled section and substantially coextensive therewith.

18. A device according to claim 2, wherein the hose forms a double-walled section and inflatable balloon means are positioned behind the double-walled section for widening the lumen before implanting the prosthesis.

19. A device according to claim 7, wherein said balloon means are independently operable for widening the lumen before implanting the prosthesis.

20. A device according to claim 8, wherein said balloon means are independently operable for widening the lumen before implanting the prosthesis.

* * * * *